United States Patent [19]

Bauer et al.

[11] Patent Number: 5,831,119
[45] Date of Patent: Nov. 3, 1998

[54] PROCESS FOR THE PREPARATION OF AMINOACETIC ACIDS WITH A TERTIARY HYDROCARBON RADICAL IN THE α-POSITION, OR THEIR NITRILES

[75] Inventors: Frank Bauer, Cologne; Wolfgang Kleemiss, Haltern; Marcel Feld, Cologne, all of Germany

[73] Assignee: Huels Aktiengesellschaft, Marl, Germany

[21] Appl. No.: 872,053

[22] Filed: Jun. 10, 1997

[30] Foreign Application Priority Data

Jun. 10, 1996 [DE] Germany .......... 196 23 141.8

[51] Int. Cl.$^6$ .................................. C07C 229/00
[52] U.S. Cl. ............................ 562/443; 562/575
[58] Field of Search ..................... 562/575, 443

[56] References Cited

PUBLICATIONS

J. March, Advanced Organic chemistry, Reactions, Mechanims, and Structure, 4th ed., pp. 1090–1091, 1992.

Toshifumi Miyazawa, et al., No. 23, pp. 51–54, "Synthesis of T–Leucine", May 31, 1979.

*Primary Examiner*—Joseph K. McKane
*Assistant Examiner*—Joseph Murray
*Attorney, Agent, or Firm*—Oblon, Spivak, McClelland, Maier & Neustadt, P.C.

[57] ABSTRACT

A process for the preparation of aminoacetic acids or aminoacetonitriles with a tertiary hydrocarbon radical in the α-position in which monoamide derivatives of malonic acid are subjected to a Hofmann rearrangement.

17 Claims, No Drawings

PROCESS FOR THE PREPARATION OF AMINOACETIC ACIDS WITH A TERTIARY HYDROCARBON RADICAL IN THE α-POSITION, OR THEIR NITRILES

BACKGROUND OF THE INVENTION

1. Field of the Invention

The invention relates to a process for the preparation of aminoacetic acids or aminoacetonitriles with a tertiary hydrocarbon radical in the α-position from α-substituted malonic acid monoamide derivatives.

2. Discussion of the Background Art

The simplest product of the present method is tert-leucine, i.e., α-tert-butylaminoacetic acid, which, as a non-proteinogenous amino acid, is of considerable importance for the synthesis of biologically active proteins with novel activity. It also serves as an auxiliary for asymmetric syntheses (see U. Schöllkopf, Pure and Applied Chem., 55 [1983], 1799). The enantiomerically pure tert-leucine required for this purpose can be obtained by the kinetic resolution of N-acyl-tert-leucine racemates with the aid of a specific deacylase (see EP 0 494 716). Furthermore, tert-leucine can easily be converted to leucinol, which is used, for example, as a chiral auxiliary for the stereoselective synthesis of insecticides (see M. L. McKennon et al., *J. Org. Chem.*, 58 [1993], 3568). Other aminoacetic acids with a tertiary hydrocarbon radical in the α-position, i.e., higher homologs of tert-leucine, may also work in a corresponding manner.

Tert-leucine can be prepared by a Strecker synthesis from pivalic aldehyde (see K. Ogura, *Bull. Chem. Soc. Jpn.*, 65 [1992], 2359) or by the ammonolysis of 2-bromo-3,3-dimethylbutyric acid (see Abderhaiden, *Z. Phys. Chem.*, 228 [1934], 193). Aminoacetic acids with other tertiary hydrocarbon radicals in the α-position can be prepared similarly from other aldehydes by a Strecker synthesis or from other bromocarboxylic acids by ammonolysis. Another known process for the preparation of tert-leucine in the L-form is the enzyme-catalyzed transamination of 3,3-dimethyl-2-oxobutyric acid (see EP 0 248 357).

Both pivalic aldehyde and 2-bromo-3,3-dimethylbutyric acid and 3,3-dimethyl-2-oxobutyric acid are relatively expensive starting materials, as are many of the aldehyde starting materials for the Strecker synthesis. Moreover, the Strecker synthesis requires hydrocyanic acid, which is demanding in terms of safety technology, and enzyme-catalyzed trans-amination gives unsatisfactory space-time yields. Accordingly, there remains a need for a process of preparing aminoacetic acid and aminoacetonitriles substituted with tertiary groups at the α-position which overcomes these disadvantages.

OBJECTS OF THE INVENTION

It is an object of the present invention to provide a process for the preparation of aminoacetic acids or aminoacetonitriles having a tertiary hydrocarbon radical substituent at the α-position, which uses inexpensive starting materials, provides high yields and avoids unsafe reagents.

SUMMARY OF THE INVENTION

These objects and others are accomplished with a process for preparing an aminoacetic acid or aminoacetonitrile by converting a malonic acid monoamide derivative substituted at the α-carbon with a tertiary hydrocarbon radical to the corresponding aminoacetic acid or aminoacetonitrile via the Hofmann rearrangement.

A more complete appreciation of the invention and many of the attendant advantages thereof will be readily obtained as the same becomes better understood by reference to the following detailed description.

DETAILED DESCRIPTION OF THE INVENTION

The process of the present invention provides a method of preparing α-substituted aminoacetic acids or aminoacetonitriles in high yield and purity from the corresponding amide derivatives by the Hofmann rearrangement. The high yields obtained with the present process are very surprising. In alkaline media substituted malonic acids are generally converted to the corresponding substituted acetic acids by decarboxylation, see F. Patai, *The Chemistry of Carboxylic Acids and Esters*, p. 589, Inter-science, New York, 1969.

As used-herein, the term "Hofmann rearrangement" refers to the reaction of a primary amide with a hypohalite salt (or a halogen and hydroxide ion) to produce the corresponding primary amine. For a general discussion of the Hofmann rearrangement, see K. P. C. Vollhardt, *Organic Chemistry*, W. H. Freeman, 1987, pp. 818–820 and J. March, *Advanced Organic Chemistry, Reactions, Mechanisms, and Structure*, Fourth Edition, John Wiley and Sons, 1992, pp. 1090–1091, both incorporated herein by reference. The conversion of tert-leucine using, for example, sodium hydroxide solution and sodium hypochlorite by the Hofmann rearrangement is illustrated below:

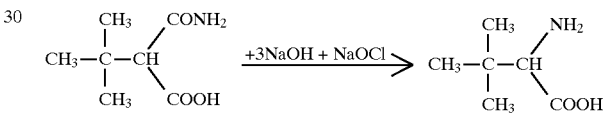

The starting materials for the present process are malonic acid monoamide, malonic acid monoester monoamide or malonomononitrile monoamides having a tertiary hydrocarbon radical substituted at the α-carbon atom. Preferably, these compounds are primary amides having the formula I:

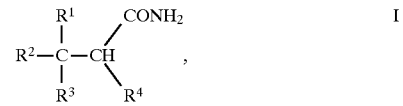

in which $R^1$, $R^2$ and $R^3$ are the same or different hydrocarbon radicals. Alternatively, any two of $R^1$, $R^2$ and $R^3$ may form a hydrocarbon ring together with the quaternary carbon atom they are bonded to. Preferably, $R^1$, $R^2$ and $R^3$ each have 1 to 20 carbon atoms. This carbon number range includes all specific values and subranges therebetween. When any two of $R^1$, $R^2$ and $R^3$ form a ring, the ring preferably contains 3 to 20 carbon atoms. The ring may be unsubstituted with hydrocarbon substituents. This carbon number range also includes all specific values and subranges therebetween.

$R^4$ may be a carboxyl, carboxylic acid ester or nitrile group. Under the conditions of the Hofmann rearrangement, a carboxylic acid ester group is usually saponified to the carboxyl group. When $R^4$ is a nitrile group, the nitrile may be hydrolyzed to the carboxylic acid. Accordingly, a nitrile starting material may provide an aminonitrile or aminoacid product, or a mixture thereof. Whether the nitrile group is preserved or hydrolyzed to the acid depends on the reaction conditions. Higher temperatures, stronger base, higher base concentration and longer reaction times, favor more hydrolysis of the nitrile group to the acid. Determining what product is formed under any particular set of reaction conditions can be accomplished by one of ordinary skill in the art. A carboxyl group may be in the form of the free carboxylate, a carboxylate metal salt or the carboxylic acid.

In the more preferred starting materials of formula I, $R^1$, $R^2$ and $R^3$ are, independently, an alkyl, alkenyl, aryl, alkaryl or aralkyl radical having up to 10 carbon atoms. Alternatively, any two of $R^1$, $R^2$ and $R^3$ may form a hydrocarbon ring having 5 to 12 carbon atoms, most preferably 5 or 6 carbon atoms, together with the quaternary carbon atom they are bonded to.

In these more preferred starting materials, $R^4$ is a carboxyl group, a nitrile group or a carboxylic acid ester group having the formula —COOR$^5$, in which $R^5$ is an alkyl radical having 1 to 4 carbon atoms, preferably 1 or 2 carbon atoms, or a benzyl radical. Even more preferably, $R^4$ is a carboxyl group.

Corresponding to the starting materials of the formula I, the reaction products preferably have the formula II:

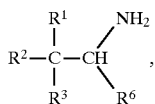

II where $R^1$, $R^2$ and $R^3$ are as defined above and $R^6$ is a carboxyl group or a nitrile group.

The starting materials of formula I may be prepared by known procedures, e.g., from cyanoacetic acid or esters thereof, by first introducing the tertiary hydrocarbon radical by reaction with appropriate electrophiles, and then hydrolyzing the nitrile group to the carboxamide group. The process of the invention can also be used to convert enantiomerically enriched or enantiomerically pure starting materials to the corresponding aminoacetic acids or aminoacetonitriles with a tertiary hydrocarbon radical in the α-position. The starting materials of formula I may also be prepared from enantiomerically enriched or enantiomerically pure malonic acid monoesters with a tertiary hydrocarbon radical in the α-position via the intermediate ester chloride. The carboxylic acids used to prepare these ester acyl chlorides may be prepared by enantioselective enzymatic hydrolysis of a corresponding diester (see the Examples). Any known enzyme which hydrolyzes carboxylic acid ester groups in aqueous media can be used as catalysts for the enzymatic partial hydrolysis. Any commercially available ester-cleaving enzymes, including esterases, lipases and proteases are suitable for this purpose. They can be used in crystalline form, in aqueous suspension or fixed to a support. Examples of suitable enzymes include porcine liver esterase, the lipase from Candida cylindracea and α-chymotrypsin, already referred to above, the papain from Carica papaya and the lipase from porcine pancreas. Enantiomerically enriched or enantiomerically pure tert-leucine can be prepared by the process of the present invention more simply than by kinetic resolution of N-acyl-tert-leucine racemates, which is quite complicated.

Examples of suitable starting materials I include, for example, α-tert-butylmalonic acid monoamide, α-tert-butylmalonic acid mononitrile monoamide (or α-tert-butylcyanoacetamide), α-tert-butylmalonic acid monomethyl ester monoamide, α-tert-pentylmalonic acid mononitrile monoamide, α-(1-methyl-1-phenylethyl) malonic acid monoamide, α-(1-methyl-1-phenylethyl) malonic acid monoethyl ester monoamide, α-(1-methylcyclohexyl)malonic acid monoamide and α-(1-methylcyclohexyl)malonic acid mononitrile monoamide.

The Hofmann rearrangement requires a base and a salt of a hypohalous acid, preferably an alkali metal hydroxide and an alkali metal hypochlorite. Preferably, the reaction is conducted in aqueous solution. Sodium hydroxide solution and sodium hypochlorite solution, also known as bleaching lye, are the most preferred reagents. Both of these materials are inexpensive and available in large quantities. The base is preferably used in amounts of 1.5 to 4 equivalents, more preferably 2 to 4 equivalents, per mol of starting material I. If I contains a nitrile group which is to be hydrolyzed, the amount of base is chosen from the upper part of the range or the reaction is carried out with an even greater excess. The salt of the hypohalous acid is preferably used in amounts of 1.0 to 1.2 equivalents per mol of starting material I.

The process according to the invention may be carried out continuously or batchwise. In the batch embodiment with sodium hydroxide as the basic substance and sodium hypochlorite as the salt of a hypohalous acid, the first step is preferably introducing I into an approximately 5 to 40 percent by weight sodium hydroxide solution. The mixture is stirred, and an approximately 5 to 15 percent by weight sodium hypochlorite solution is added gradually, the temperature preferably being kept at 0° to 20° C. To complete the reaction, the mixture is heated to a higher temperature, e.g., up to 180° C., and allowed to react further for some time, e.g., 1 to 6 hours. In general the reaction is complete after the reaction mixture has been heated for 1 to 2 hours at 60° to 80° C. After cooling, the reaction mixture is preferably neutralized to a pH of about 6 to about 8, preferably with a mineral acid, such as hydrochloric acid or sulfuric acid, to give an aqueous solution which, as the reaction product, contains the desired substituted aminoacetic acid or aminoacetonitrile and the salt comprising the cation of the hypohalite salt and the conjugate based of the acid used to neutralize the reaction mixture. This salt by-product can be separated from the reaction product by one of the known ion exchange and/or membrane processes and then the salt-free solution can be concentrated to dryness. Alternatively, the neutralized reaction mixture containing the desired reaction product and the salt by-product may be evaporated to dryness without prior separation of the salt. Then, the evaporation residue can be extracted with a suitable solvent selective for the substituted aminoacetic acid or aminoacetonitrile product, e.g. boiling methanol. The bulk of the salt by-product is left behind, undissolved. When the selective solvent is evaporated from the extract, the substituted aminoacetic acid or aminoacetonitrile is obtained as the residue. Depending on the salt by-product and the selective solvent used, the reaction product may still contain 10 to 20 percent by weight of the salt and may be farther purified by ion exchange and/or membrane processes.

The starting material I may also be reacted in situ in the present process, starting directly from the reaction mixture obtained in the partial hydrolysis/saponification of the appropriately substituted cyanoacetic acid or one of its esters to the malonic acid monoamide in a basic medium. In this case it is necessary to add only about 1.5 to 2.5 equivalents of base and to carry out the Hofmann rearrangement, including the working-up, as described above.

The process according to the invention can also be carried out continuously, e.g., analogous to the procedure described in DE-OS 44 41 777, incorporated herein by reference. In this embodiment, a mixture of starting material I and alkali metal hydroxide solution is brought into contact with a hypochlorite solution continuously at 10° to 180° C., preferably 40° to 80° C., for a sufficient length of time, and then the reaction mixture is worked up continuously or batchwise as described above.

In all the process variants, the aminoacetic acids or aminoacetonitriles with a tertiary hydrocarbon radical in the α-position may be obtained with high space-time yields and with reaction yields generally of 90% of theory, or more. By recrystallizing the products, e.g., from water, they are obtained in high purity, e.g., of more than 98% in the case of tert-leucine.

Having generally described this invention, a further understanding can be obtained by reference to certain specific examples which are provided herein for purposes of illustration only and are not intended to be limiting unless otherwise specified.

EXAMPLES

A. Preparation of Starting Materials

Example 1

3.0 g (13.9 mmol) of diethyl α-tert-butylmalonate are suspended in a mixture of 10 ml of 0.1M aqueous potassium dihydrogen phosphate solution and 15 ml of 0.1M aqueous disodium hydrogen phosphate solution. 1.3 ml of Chirazyme E1 (Boehringer Mannheim GmbH) are added to the suspension. The pH is monitored and 1N sodium hydroxide solution is metered slowly into the stirred suspension, kept at room temperature, so that the pH is in the range 6 to 9. 13 ml (13 mmol) of 1N sodium hydroxide solution are consumed over 48 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 2.35 g (12.5 mmol) of monoethyl α-tertbutylmalonate, corresponding to a yield of 90% of theory. The enantiomeric excess is 96%.

Example 2

533 mg (2.83 mmol) of dimethyl α-tert-butylmalonate are suspended in a mixture of 5 ml of 0.1M aqueous potassium dihydrogen phosphate solution and 7.5 ml of 0.1M aqueous disodium hydrogen phosphate solution. 0.3 ml of porcine liver esterase (Boehringer Mannheim GmbH, catalog no. 104698) is added to the suspension. The pH is monitored and 1N sodium hydroxide solution is metered slowly into the stirred suspension, kept at room temperature, so that the pH is in the range 6 to 9. 2.9 ml (2.9 mmol) of 1N sodium hydroxide solution are consumed over 24 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 432 mg (2.48 mmol) of monomethyl α-tert-butylmalonate, corresponding to a yield of 85% of theory. The enantiomeric excess is 89%.

Example 3

500 mg (2.17 mmol) of diethyl α-tert-pentylmalonate are suspended in a mixture of 5 ml of 0.1M aqueous potassium dihydrogen phosphate solution and 7.5 ml of 0.1M aqueous disodium hydrogen phosphate solution. 0.3 ml of porcine liver esterase (Boehringer Mannheim GmbH, catalog no. 104698) is added to the suspension. The pH is monitored and 1N sodium hydroxide solution is metered slowly into the stirred suspension, kept at room temperature, so that the pH is in the range 6 to 9: 2.2 ml (2.2 mmol) of 1N sodium hydroxide solution are consumed over 24 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 334 mg (1.65 mmol) of monoethyl α-tertpentylmalonate, corresponding to a yield of 75% of theory. The enantiomeric excess is 82%.

Example 4

454 mg (1.67 mmol) of diethyl α-(1-methyl-1-phenylethyl)malonate are suspended in a mixture of 5 ml of 0.1M aqueous potassium dihydrogen phosphate solution and 7.5 ml of 0.1M aqueous disodium hydrogen phosphate solution. 0.4 ml of porcine liver esterase (Boehringer Mannheim GmbH, catalog no. 104698) is added to the suspension. The pH is monitored and 1N sodium hydroxide solution is metered slowly into the stirred suspension, kept at room temperature, so that the pH is in the range 6 to 9. 1.7 ml (1.7 mmol) of 1N sodium hydroxide solution are consumed over 24 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 340 mg (1.35 mmol) of monoethyl α-(1-methyl-1-phenylethyl)malonate, corresponding to a yield of 81% of theory. The enantiomeric excess is 94%.

Example 5

533 mg (2.83 mmol) of dimethyl α-tert-butylmalonate are suspended in a mixture of 10 ml of 0.1M aqueous potassium dihydrogen phosphate solution and 15 ml of 0.1M aqueous disodium hydrogen phosphate solution. 0.4 ml of porcine liver esterase (Boehringer Mannheim GmbH, catalog no. 104698) is added to the suspension. The pH is monitored and 1N sodium hydroxide solution is metered slowly into the stirred suspension, kept at room temperature, so that the pH is in the range 6 to 9. 2.8 ml (2.8 mmol) of 1N sodium hydroxide solution are consumed over 30 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 432 mg (2.48 mmol) of monomethyl α-tert-butylmalonate, corresponding to a yield of 87% of theory. The enantiomeric excess is 89%.

Example 6

476 mg (1.9 mmol) of dimethyl α-(1-methyl-1-phenylethyl)malonate are suspended in a mixture of 10 ml of 0.1M aqueous potassium dihydrogen phosphate solution and 15 ml of 0.1M aqueous disodium hydrogen phosphate solution. 0.5 ml of porcine liver esterase (Boehringer Mannheim GmbH, catalog no. 104698) is added to the suspension. The pH is monitored and 1N sodium hydroxide solution is metered slowly into the stirred suspension, kept at room temperature, so that the pH is in the range 6 to 9. 1.6 ml (1.6 mmol) of 1N sodium hydroxide solution are consumed over 30 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 305 mg (1.29 mmol) of monomethyl α-(1-methyl-1-phenylethyl)malonate, corresponding to a yield of 68% of theory. The enantiomeric excess is 90%.

Example 7

500 mg (1.9 mmol) of dimethyl α-(1-methylcyclohexyl) malonate are suspended in a mixture of 10 ml of 0.1M aqueous potassium dihydrogen phosphate solution and 15 ml of 0.1M aqueous disodium hydrogen phosphate solution. 0.5 ml of porcine liver esterase (Boehringer Mannheim GmbH, catalog no. 104698) is added to the suspension. The pH is monitored and 1N sodium hydroxide solution is metered slowly into the stirred suspension, kept at room temperature, so that the pH is in the range 6 to 9. 1.9 ml (1.9 mmol) of 1N sodium hydroxide solution are consumed over 40 hours. The reaction mixture is then acidified with concentrated hydrochloric acid (pH 1–2) and filtered on Celite. The reaction product is extracted several times with diethyl ether and the ether phase is dried over magnesium sulfate. Removal of the solvent leaves 400 mg (1.76 mmol) of monomethyl α-(1-methylcyclohexyl)malonate, corresponding to a yield of 90% of theory. The enantiomeric excess is 96%.

B. Preparation of Reaction Products

Example 8

50 g (0.125 mol) of 10 percent by weight sodium hydroxide solution are placed in a stirred vessel at room temperature. 20 g (0.125 mol) of α-tert-butylmalonic acid monoamide are added, the mixture being stirred and cooled to 10° C. A further 50 g (0.25 mol) of 20 percent by weight sodium hydroxide solution are then added, with stirring, the temperature being kept at <15 ° C. 83.8 g (0.125 mol) of 11.1 percent by weight sodium hypochlorite solution are then metered in, still at a temperature of <15° C., and the mixture is stirred for 3 hours at this temperature. It is subsequently heated at 60° C. for 3 hours and then cooled to room temperature. The reaction mixture is then adjusted to a pH of 7 with concentrated hydrochloric acid and evaporated to dryness. The residue is extracted with 500 g of boiling methanol. According to elemental analysis, the 16 g of tert-leucine which remain after concentration of the methanolic solution still contain ca. 1.5 g of sodium chloride. The yield of tert-leucine is 98% of theory, allowing for the sodium chloride still present.

Example 9

160 g (0.8 mol) of 20 percent by weight sodium hydroxide solution are placed in a stirred vessel at 50° C. and stirred. 127.4 g (0.8 mol) of α-tert-butylmalonic acid monoamide are added, the mixture being stirred and cooled to 10° C. A further 320 g (1.6 mol) of 20 percent by weight sodium hydroxide solution are then added, with stirring, the temperature being kept at <15° C. 536.2 g (0.8 mol) of 11.1 percent by weight sodium hypochlorite solution are then metered in over 40 minutes, still at a temperature of<15° C. The mixture is subsequently heated at 60° C. for 3 hours and then cooled to room temperature. The reaction mixture is then adjusted to a pH of 7 with concentrated hydrochloric acid and concentrated to dryness to give ca. 340 g of dry residue, which is extracted with 1000 g of boiling methanol. According to elemental analysis, the 100 g of tert-leucine which remain after concentration of the methanolic solution still contain ca. 20 g of sodium chloride. The yield of tert-leucine is 95% of theory, allowing for the sodium chloride still present.

Obviously, numerous modifications and variations of the present invention are possible in light of the above teachings. It is therefore to be understood that within the scope of the appended claims, the invention may be practiced otherwise than as specifically described herein.

This application is based on German Patent Application No. 196 23 141.8, filed Jun. 10, 1996 and incorporated herein by reference in its entirety.

What is claimed as new and desired to be secured by Letters Patent of the United States is:

1. A process for preparing an aminoacetic acid, comprising:
reacting a malonic acid monoamide, a malonic acid monoester monoamide or malonomononitrile monoamide having a tertiary hydrocarbon substituent at the α-carbon atom with a base and a salt of a hypohalous acid, thereby providing an aminoacetic acid product in a yield of at least 90% of the theoretical yield.

2. The process of claim 1, wherein said malonic acid monoamide, malonic acid monoester monoamide or malonomononitrile monoamide has formula I:

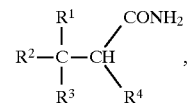

and said aminoacetic acid has formula II:

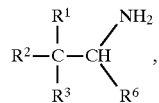

wherein
$R^1$, $R^2$ and $R^3$ are each, independently, a hydrocarbon radical, or two of $R^1$, $R^2$ and $R^3$ form a hydrocarbon ring together with the quaternary carbon atom they are bonded to,
$R^4$ is a carboxyl, carboxylic acid ester or nitrile group; and
$R^6$ is a carboxyl group.

3. The process of claim 2, wherein
$R^1$, $R^2$ and $R^3$ are each, independently, an alkyl, alkenyl, aryl, alkaryl or aralkyl radical having up to 10 carbon atoms, or
two of $R^1$, $R^2$ and $R^3$ form a hydrocarbon ring having 5 to 12 carbon atoms together with the quaternary carbon atom they are bonded to; and
$R^4$ is a carboxyl group, a nitrile group or a carboxylic acid ester group having the formula —$COOR^5$, wherein $R^5$ is an alkyl radical having 1 to 4 carbon atoms or a benzyl radical.

4. The process of claim 2, wherein $R^4$ is a carboxyl or carboxylic acid ester group and $R^6$ is a carboxyl group.

5. The process of claim 2, wherein $R^4$ is a nitrile group and $R^6$ is a carboxyl group.

6. The process of claim 1, wherein said base is an alkali metal hydroxide and said salt of a hypohalous acid is an alkali metal hypohalite.

7. The process of claim 2, wherein said compound of formula I is α-tert-butylmalonic acid monoamide, α-tert-butylmalonic acid mononitrile monoamide, α-tert-butylmalonic acid monomethylester monoamide, α-tert-pentylmalonic acid mononitrile monoamide, α-(1-methyl-1-phenylether)malonic acid monoamide, α-(1-methyl-1-phenylethyl)malonic acid monoethylester monoamide, α-(1-methylcyclohexyl)malonic acid monoamide or α-(1-methylcyclohexyl)malonic acid mononitrile monoamide.

8. The process of claim 6, wherein said alkali metal hydroxide is sodium hydroxide and said alkali metal hypohalite is sodium hypochlorite.

9. The process of claim 2, wherein said compound of formula I is contacted with 1.5 to 4 equivalents of sodium hydroxide in an aqueous reaction mixture, followed by adding 1.0 to 1.2 equivalents of sodium hypochlorite solution at a temperature of 0° to 20° C., followed by heating at a temperature of 20° to 180° C.

10. The process of claim 1, which is a continuous or batch process.

11. The process of claim 1, further comprising:
neutralizing the reaction mixture with a mineral acid;
evaporating to dryness; and
isolating said aminoacetic acid by extraction with a solvent.

12. The process of claim 11, wherein said solvent is methanol.

13. The process of claim 1, further comprising:
neutralizing the reaction mixture with a mineral acid; and
purifying the aminoacetic acid by an ion exchange process and/or a membrane process.

14. A process for preparing an aminoacetic acid comprising contacting a base and a hypohalite salt with a compound of formula I:

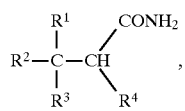

wherein $R^1$, $R^2$ and $R^3$ are each, independently, a hydrocarbon radical, or two of $R^1$, $R^2$ and $R^3$ form a hydrocarbon ring together with the quaternary carbon atom they are bonded to, $R^4$ is a carboxyl, carboxylic acid ester or nitrile group; and $R^6$ is a carboxyl group.

15. The process of claim 14, wherein said base is an alkali metal hydroxide.

16. The process of claim 14, wherein said hypohalite salt is an alkali metal hypohalite.

17. The process of claim 14, wherein the contacting step is conducted in an aqueous reaction mixture.

* * * * *